United States Patent [19]

Faers et al.

[11] Patent Number: 5,389,665
[45] Date of Patent: Feb. 14, 1995

[54] FUNGICIDAL FORMULATIONS

[75] Inventors: Malcom A. Faers, Cambridge, England; Zoltan Damo, Esppstein, Germany

[73] Assignee: Schering Agrochemicals Limited, Cambridge, England

[21] Appl. No.: 119,085

[22] PCT Filed: Mar. 3, 1992

[86] PCT No.: PCT/GB92/00375

§ 371 Date: Jan. 24, 1994

§ 102(e) Date: Jan. 24, 1994

[87] PCT Pub. No.: WO92/16105

PCT Pub. Date: Oct. 1, 1992

[30] Foreign Application Priority Data

Mar. 19, 1991 [DE] Germany .................. 4108871

[51] Int. Cl.$^6$ ............... A01N 25/04; A01N 47/38
[52] U.S. Cl. ....................... 514/399; 548/334.1
[58] Field of Search ................ 548/334.1; 514/399

[56] References Cited

U.S. PATENT DOCUMENTS 3,991,071 11/1976 Brookes et al. ............... 548/334.1
4,044,118 8/1977 McCoy et al. ................ 424/200

FOREIGN PATENT DOCUMENTS 357559 7/1990 European Pat. Off. .
2059773 4/1981 United Kingdom .

OTHER PUBLICATIONS

World Patents Index Latest Week 8132 (Jun. 22, 1981) AN-81-57762D & JP, A, 56 075 409.

*Primary Examiner*—Richard L. Raymond
*Attorney, Agent, or Firm*—Ostrolenk, Faber, Gerb & Soffen

[57] ABSTRACT

The invention provides liquid formulation, which comprises 0.1 to 75% by weight of prochloraz, at least 3% by weight of a nonionic surfactant or surfactant mixture, at least 8.5% by weight of a phenol derivative to prevent crystallization of the prochloraz on storage of the emulsion, said phenol being a compound of formula $$R^1-O-X$$

in which $R^1$ is phenyl, substituted by one to three $C_1$–$C_8$-alkyl, $\alpha$-methylbenzyl or $\alpha$-methyl-4-methylbenzyl groups, by 4-hydroxyphenylene in the para-position, a $C_6$–$C_{22}$-alkyl group in the para-position or by two $C_3$–$C_{12}$-alkyl groups in the ortho and para-positions, and X is hydrogen, an alkali metal, an alkaline earth metal or $NR_3$ in which each R is the same or different and is hydrogen or $C_1$–$C_8$-alkyl, optionally substituted by hydroxy, and at least 1% by weight of an organic solvent which is only slightly soluble in water and which comprises at least one aromatic hydrocarbon.

13 Claims, No Drawings

FUNGICIDAL FORMULATIONS

FIELD OF THE INVENTION

The present invention relates to new formulations of prochloraz, a known fungicide.

Prochloraz is the common name for the fungicide having the chemical name N-propyl-N-[2-(2,4,6-trichlorophenoxy)ethyl]imidazole-1-carboxamide. The commercial product is most commonly formulated as an emulsifiable concentrate in which the compound, dissolved in an inflammable solvent, such as xylene, is in admixture with various emulsifying and wetting agents. This concentrate is then diluted with water by the user, e.g. for spraying onto crops. It clearly would be an advantage, especially from the safety point of view, if at least some of the inflammable solvent could be replaced by water. One way of achieving this would be to have a concentrate consisting of an emulsion comprising a solution of prochloraz in a reduced amount of water immiscible solvent which is emulsified in water. The problem with such formulations is that the prochloraz solvent phase is generally supersaturated and the prochloraz tends to crystallise on standing. Such a formulation cannot be reconstituted to a product of uniform concentration so that even if the user can remove the crystals, which would otherwise rapidly clog up spraying apparatus, he is left with a formulation which cannot be applied uniformly to his crop and is therefore wholly unacceptable.

In EP 357559, there are disclosed aqueous formulations of pesticides which have a very low solubility in water. The formulation consists of an aqueous emulsion and contains particular phenols in order to stabilise the emulsion and prevent crystallisation of the pesticide. A particular advantage given for this patent application is the complete absence of organic solvent in the formulation. We have found, however, that in the case of prochloraz, a total absence of hydrocarbon solvent does not give a satisfactory formulation.

According to the present invention, there is provided a liquid formulation which comprises 0.1 to 75% by weight of prochloraz, at least 3%, preferably 5 to 15%, by weight, of a surfactant or surfactant mixture, at least 8.5%, preferably at least 9.5%, by weight of a phenol derivative to prevent crystallisation of the prochloraz on storage of the formulation, said phenol being of formula

in which $R^1$ is phenyl, substituted by one to three $C_1$-$C_8$-alkyl, α-methylbenzyl or α-methyl-4-methylbenzyl groups, by 4-hydroxyphenylene in the pare-position, a $C_6$-$C_{22}$-alkyl group in the pare-position or by two $C_3$-$C_{12}$-alkyl groups in the ortho and pare-positions, and X is hydrogen, an alkali metal, an alkaline earth metal or $NR_3$ in which each R is the same or different and is hydrogen or $C_1$-$C_8$-alkyl, optionally substituted by hydroxy, and at least 1, preferably 5 to 10%, by weight of an organic solvent which is only slightly soluble in water and which comprises at least one aromatic hydrocarbon.

The invention is particularly applicable to aqueous based emulsion formulations.

The invention can also be applied to other formulations, such as microemulsions, emulsifiable concentrates and mixed systems in which for example a second particulate active ingredient is dispersed in the microemulsion or emulsifiable concentrate.

The preferred formulations are two-phase systems of either oil in water or water in oil. In the especially preferred oil in water formulations, the water is the carrier phase and the insoluble oily phase exists in one or more organic solvents in the form of tiny droplets which contain the dissolved prochloraz surrounded by surfactant molecules. The crystallisation inhibiting phenol derivative is also in the oily phase. The usual additives for formulations of this type are also found in the aqueous phase or in the oil phase depending on their solubility.

The content of prochloraz is preferably 10-60% by weight of the formulation.

If desired the compositions can include other pesticides, especially other fungicides, e.g. triazole fungicides, such as cyproconazole, morpholine fungicides, such as fenpropimorph or fenpropidin, and other fungicides typically co-formulated with prochloraz, including carbendazim.

The formulation of the invention contains in the oily phase an organic solvent that is only slightly soluble or miscible with water, the content of which is in general from 1-60%, preferably 3-30%, especially 5-10%, by weight of the formulation. Suitable solvents are aromatic hydrocarbons, such as alkylbenzenes, for example xylene, toluene, trimethylbenzenes, methylethylbenzenes, dimethylethyl-benzenes, diethylbenzenes, tetramethylbenzenes, pentamethylbenzenes, 1,2-methylnaphthalenes, derivatives of these compounds or mixtures of aromatic hydrocarbons, such as those having the trade mark Solvesso (produced by Esso) or Shellsol (produced by Shell).

The surfactants used in the formulations are generally nonionic surfactants and examples of these include ethoxylated saturated and unsaturated fatty alcohols or mixtures of fatty alcohols of 8-24, preferably 12-20, carbon atoms, which generally comprise 10-60 ethylene oxide units. Generally these surfactants comprise a mixture of ethoxylated alcohols in which the number of ethylene oxide units can vary, i.e. they comprise various length polyglycol ether chains, and/or the chain length of the fatty alcohols can vary. Suitable compounds are e.g. derivatives of oleyl alcohol, lauryl alcohol, stearyl alcohol and coconut fat oil alcohol. Other suitable surfactants are triglycerides of saturated or unsaturated $C_8$-$C_{24}$, especially $C_{12}$-$C_{20}$, fatty alcohols which are ethoxylated with 10-60, especially 20-45 ethylene oxide units and are obtained for example by ethoxylation of plant oils, such as palm oil or castor oil. Surfactants of this type are sold under the trade name Emulsogen EL (Hoechst).

Further suitable nonionic surfactants are propylene oxide-ethylene oxide block co-polymers of the formula

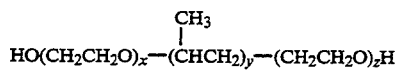

in which x, y and z are such that the polymer has a molecular weight of over 1000. Generally a mixture of surfactants of this type are used in which x, y and z vary. These compound are formed by interaction of ethylene oxide with polypropylene glycols.

Still further suitable nonionic surfactants are phenolic compounds of the formula

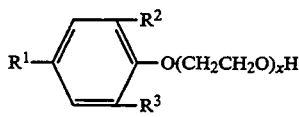

in which $R^1$ is a branched or straight chain $C_4$–$C_{15}$-alkyl, preferably $C_4$–$C_{10}$-alkyl, group of, $R^2$ and $R^3$ are hydrogen or have the same meaning as $R^1$ and in which $R^1$, $R^2$ and $R^3$ may be the same or different, and x is 4–60, preferably 8–30. In practice a mixture of such compounds is generally used in which the number of the ethylene oxide units varies, for example nonylphenol with 4–30 ethylene oxide units and tributylphenol with 4–50 ethylene oxide units. Phenolic compounds in which $R^2$ and $R^3$ are both hydrogen and $R^1$ is $C_4$–$C_{15}$-alkyl, are sold under the trade name Arkopal (Hoechst) and those in which $R^1$, $R^2$ and $R^3$ are $C_1$–$C_5$-alkyl, are sold under the trade name Sapogenat (Hoechst).

The surfactant is preferably one of
a) an ethoxylated fatty alcohol of formula R—CH$_2$—O—(CH$_2$CH$_2$))$_x$H, in which R is a $C_7$–$C_{23}$-alkyl group and x is 10 to 60,
b) a substituted triglyceride or triglyceride mixture of 10 to 60 ethylene oxide units, especially an ethoxylated plant oil,
c) a propylene oxide-ethylene oxide block-copolymer,
d) a phenolethoxylate of formula

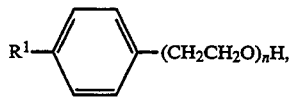

in which group $R^1$ is a $C_{4-15}$-alkyl and n is 4 to 60, or a mixture of these.

However the formulations can comprise other surfactants commonly used in the art. Thus anionic surfactants may be in a blend with nonionic surfactant(s).

Anionic compounds include for example, sulphonates such as alkylaryl sulphonates or petroleum sulphonates; sulphates such as alcohol sulphates or other sulphates; phosphate esters; or sulphosuccinates.

The amount of surfactant is generally from 3–40%, preferably 5–15% by weight.

The amount of the phenol derivative is preferably 10 to 30% by weight of the formulation.

The particularly preferred phenol derivatives are butylphenols, especially o-sec.-butylphenol.

Besides these, the formulation can optionally contain conventional additives for agrochemical formulations in the usual amounts, such as for example thickeners, emulsion stabilisers, dyestuffs, preservatives, anti-foaming agents or anti-freezes.

Thickeners help to raise the viscosity of emulsions. Examples include natural, linear high molecular weight polysaccharides, especially xanthan gum, which is formed essentially from the mannose and glucose and glucuronic acid salts and having a molecular weight of around 2 million, and aluminium silicates.

Dyestuffs can be azo dyes or phthalocyanine dyes.

Examples of preservatives are 2-hydroxybiphenyl, sorbic acid and 1,2-benzisothiazolin-3-one, and silicone oils are examples of antifoaming agents.

Examples of anti-freezes are polyglycols, polyols such as glycerine, ethylene glycol and propylene glycol and urea. They are optionally present in an amount of up to 10% by weight of emulsions.

Emulsion stabilisers are well known and are generally polymeric products, e.g. polyvinyl alcohol/polyvinyl acetate copolymers.

Water generally comprises 20 to 50% by weight of the formulation.

The preparation of aqueous emulsions according to the invention can be carried out preferably by adding the organic phase, comprising a mixture of organic solvent, surfactant, crystallisation inhibitor and the active ingredient to water. In order to achieve uniform separation of droplets the mixture is suitably submitted to strong shearing forces for example by milling with a colloidal mill (DE-A-3 319 796), a statistical mixer or an ultramixer (for example Ultraturax, produced by IKA, Germany). The mixing can be carried out over a wide temperature range for example between 0 and 80, especially 10° to 60° C. The process can be carried out in a simple, quick and cost effective manner.

In the resulting finely divided emulsion, the drops in the water generally have an average size of 1 to 3 μm.

The formulation of the invention can be used as such or more usually is applied to the locus of the fungus, e.g. to a plant or seed after suitable dilution with water. The dilution depends on the concentration of the prochloraz and the individual particular indication. The formulation is storage and use stable over a temperature range of between −10° and 50° C. over several months; that means it remains chemically and physically unchanged and shows no crystallisation. It also has good high and low temperature stability.

The invention is illustrated by the following Examples.

EXAMPLE 1

Prochloraz is stirred at room temperature with a mixture of Emulsogen EL 400 (ethoxylated plant oil, Hoechst) as the non-ionic surfactant, Solvesso 200 (methylnaphthalene fraction, Esso) as organic solvent and o-sec.-butylphenol as crystallisation inhibiting compound in various amounts. The resulting homogenous solution was added with stirring to water. In two formulations (Nos 5 and 6) xanthan gum (Kelzan from Kelco) was added as a thickener. The amount of solvent and phenol is shown in the table.

The emulsions were stored for 12 weeks at a temperature of −5° to 10° C. and their stability, especially their crystal formation was observed. In order to accelerate crystal formation some samples of the emulsions were seeded with active ingredient crystals.

For the purposes of comparison, formulations were prepared with no or lesser amounts of o-sec-phenol.

TABLE

| | Formulation No | | | | | |
|---|---|---|---|---|---|---|
| (invention) | 1 | 2 | 3 | 4 | 5 | 6 |
| Solvent (% w/w) | 7.1 | 6.2 | 5.3 | 4.5 | 8.9 | 7.1 |
| o-sec-butylphenol (% w/w) | 10.7 | 11.6 | 12.5 | 13.4 | 8.9 | 10.7 |
| (comparison) | 7 | 8 | 9 | 10 | 11 | 12 |
| Solvent (% w/w) | 18.0 | 13.4 | 17.0 | 16.2 | 15.1 | 14.3 |
| o-sec-butylphenol (% w/w) | 0 | 0* | 0.9 | 1.8 | 2.7 | 3.6 |
| (comparison) | 13 | 14 | 15 | 16 | | |
| Solvent (% w/w) | 13.5 | 12.6 | 11.7 | 9.9 | | |
| o-sec-butylphenol | 4.5 | 5.4 | 6.3 | 8.1 | | |

TABLE-continued

| | Formulation No |
|---|---|
| (% w/w) | |

* = includes 4.5% nonylphenolethoxylate

With formulations of the invention no crystals of active ingredient formed. In the comparison formulations crystallisation occurred, at −5° C., after only 2 weeks and at 0°, 5° and 10° C. at the latest, after 4 weeks. In the non-seeded comparative formulations, crystallisation of the active ingredient occurred at −5° after 8 weeks and at 0° C. after 12 weeks.

Thus even though the comparison formulations comprised more solvent than formulations of the invention, lack of sufficient phenol allowed crystallisation to occur. The presence of at least 8.5% of the phenol is thus essential in formulations of this type.

EXAMPLE 2

Oil in water emulsion formulations were prepared by mixing the following ingredients:

| | % w/v | |
|---|---|---|
| | A (invention) | B (comparison) |
| prochloraz | 45 | 45 |
| nonylphenolethoxylate | 2.5 | 2.5 |
| ethylene oxide-propylene oxide block copolymer | 3 | 3 |
| Proxel XL2⁴ | 2 | 2 |
| Propylene glycol | 6.5 | 6.5 |
| o-sec-butylphenol | 15 | 15 |
| polyvinyl alcohol | 2 | 2 |
| Solvesso 200 | 5 | 0 |
| water | to 100 | to 100 |

The formulations were treated and stored in a similar manner to Example 1. After 3 months under all conditions, the formulation of the invention showed no evidence of crystal formation, whereas in the comparison formulation containing no hydrocarbon solvent, unacceptable amounts of crystals had formed in formulations seeded and stored at −5°.

We claim:

1. A liquid formulation, which comprises 0.1 to 75% by weight of prochloraz, at least 3% by weight of a nonionic surfactant or surfactant mixture, at least 8.5% by weight of a phenol derivative to prevent crystallisation of the prochloraz on storage of the emulsion, said phenol being a compound of formula $$R^1\text{---}O\text{---}X$$

in which $R^1$ is phenyl, substituted by one to three $C_1$-$C_8$alkyl, α-methylbenzyl or α-methyl-4-methylbenzyl groups, by 4-hydroxyphenylene in the para-position, a $C_6$-$C_{22}$-alkyl group in the para-position or by two $C_3$-$C_{12}$-alkyl groups in the ortho and para-positions, and X is hydrogen, an alkali metal, an alkaline earth metal or $NR_3$ in which each R is the same or different and is hydrogen or $C_1$-$C_8$-alkyl, optionally substituted by hydroxy, and at least 1% by weight of an organic solvent which is only slightly soluble in water and which comprises at least one aromatic hydrocarbon.

2. A formulation according to claim 1, which is an aqueous emulsion.

3. A formulation according to claim 1, which comprises 5 to 15% by weight of surfactant.

4. A formulation to claim 1, which comprises at least 9.5% by weight of the phenol.

5. A formulation according to claim 4, which comprises 10 to 30% by weight of the phenol.

6. A formulation according to claim 5, which comprises 10-60% by weight of prochloraz.

7. A formulation according to claim 6, which comprises 3-40% by weight of surfactant.

8. A formulation according to claim 7, which comprises 5-15% by weight of surfactant.

9. A formulation according to claim 8, in which the surfactant is a) an ethoxylated fatty alcohol of formula R—CH$_2$—O—(CH$_2$CH$_2$O)$_x$H, in which R is a $C_7$-$C_{23}$-alkyl group and x is 10 to 60, b) a substituted triglyceride or triglyceride mixture of 10 to 60 ethylene oxide units, especially an ethoxylated plant oil, c) a propylene oxide-ethylene oxide block-copolymer, or d) a phenolethoxylate of formula

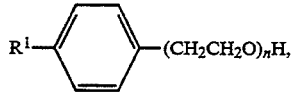

$R^1$—⟨phenyl⟩—(CH$_2$CH$_2$O)$_n$H, in which group $R^1$ is a $C_{4-15}$-alkyl and n is 4 to 60, or a mixture of these.

10. A formulation according to claim 9, which comprises 20 to 50% by weight of water.

11. A formulation according to claim 2, which comprises 5 to 15% by weight of surfactant.

12. A formulation to claim 2, which comprises at least 9.5% by weight of the phenol.

13. A formulation of claim 3, which comprises at least 9.5% by weight of the phenol.

* * * * *